PESTICIDAL THIONOPHOSPHORIC ACID AMINE ESTERS

[75] Inventors: Herbert Sommer, Remscheid; Dieter Arlt, Cologne; Jürgen Hartwig, Leverkusen; Bernhard Homeyer, Leverkusen; Hans-Detlef Matthaei, Leverkusen, all of Fed. Rep. of Germany

[73] Assignee: Bayer Aktiengesellschaft, Leverkusen, Fed. Rep. of Germany

[21] Appl. No.: 327,490

[22] Filed: Mar. 23, 1989

[30] Foreign Application Priority Data

Mar. 31, 1988 [DE] Fed. Rep. of Germany ....... 3811006

[51] Int. Cl.$^5$ ............................ A01N 9/36; C07D 9/24
[52] U.S. Cl. ..................................... 514/137; 558/199
[58] Field of Search .......................... 558/199; 514/137

[56] References Cited

U.S. PATENT DOCUMENTS 4,104,377  8/1978  Arlt et al. ............................. 558/204
4,159,324  6/1979  Arlt et al. ............................. 558/199

FOREIGN PATENT DOCUMENTS 0001053  3/1979  European Pat. Off. .
2356660  1/1978  France .

Primary Examiner—Cecilia Shen
Attorney, Agent, or Firm—Sprung Horn Kramer & Woods

[57] ABSTRACT

Pesticidal thionophosphoric acid amide esters of the formula

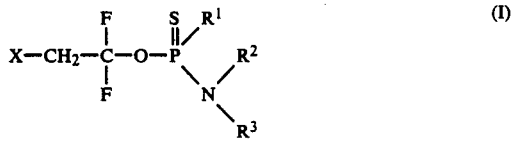

in which
$R^1$ stands for optionally substituted radicals from the group consisting of alkoxy, alkenyloxy and alkinyloxy,
$R^2$ and $R^3$ are identical or different and independently of one another stand for hydrogen or for optionally substituted radicals from the group consisting of alkyl, cycloalkyl, alkenyl and alkinyl, or together with the nitrogen atom to which they are bonded form a 5- to 7-membered ring, and
X stands for halogen.

Intermediates of the formulae

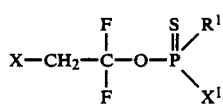

and

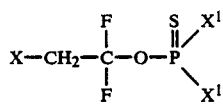

in which $X^1$ is halogen, are also new.

13 Claims, No Drawings

PESTICIDAL THIONOPHOSPHORIC ACID AMINE ESTERS

The invention relates to new thionophosphoric acid amide esters, a process for their preparation, their use as pesticides, in particular as insecticides, acaricides and nematicides, and new intermediates and a process for the preparation of such intermediates.

It has already been disclosed that certain thionophosphoric(phosphonic)acid amide esters, such as, for example, O-methyl O-(2-chloro-1-fluoro-ethyl) thionophosphoramidate, have pesticidal activity (cf. DE-OS (German Published Specification) No. 2,629,016, corresponding to U.S. Pat. No. 4,159,324). However, the action and the duration of action of these known compounds are not always completely satisfactory, in particular at low application rates or low concentrations of active compound.

New thionophosphoric acid amide esters of the general formula $$\begin{array}{c} F \quad\ S \quad R^1 \\ | \quad\ \| \;/ \\ X-CH_2-C-O-P \quad\ R^2 \\ | \quad\quad\quad \backslash\;/ \\ F \quad\quad\quad N \\ \quad\quad\quad\quad\quad \backslash R^3 \end{array} \quad (I)$$

have now been found,
in which formula $R^1$ stands for optionally substituted radicals from the series comprising alkoxy, alkenyloxy and alkinyloxy, $R^2$ and $R^3$ are identical or different and independently of one another stand for hydrogen and for optionally substituted radicals from the series comprising alkyl, cycloalkyl, alkenyl or alkinyl, or together with the nitrogen atom to which they are bonded form a 5- to 7-membered, saturated or unsaturated ring and X stands for halogen.

The compounds of the formula (I) possess an asymmetrically substituted phosphorus atom. Thus, they can be present in various optical isomer forms which can be obtained in amounts of varying ratios. In all cases, they are mainly present as racemates. The invention relates both to the isomer mixtures and to the individual isomers.

Furthermore, it has been found that the new thionophosphoric acid amide esters of the formula (I) are obtained when O-(1,1-difluoro-2-halogeno-ethyl) halogenothionophosphates of the formula $$\begin{array}{c} F \quad\ S \quad R^1 \\ | \quad\ \| \;/ \\ X-CH_2-C-O-P \\ | \quad\quad\quad \backslash \\ F \quad\quad\quad X^1 \end{array} \quad (II)$$

in which

X and $R^1$ have the abovementioned meanings and $X^1$ stands for halogen, preferably chlorine, are reacted with amines of the formula $$\begin{array}{c} R^2 \\ / \\ HN \\ \backslash \\ R^3 \end{array} \quad (III)$$

in which $R^2$ and $R^3$ have the abovementioned meanings, if appropriate in the presence of a diluent and if appropriate in the presence of an acid acceptor.

The new thionophosphoric acid amide esters of the formula (I) are distinguished in an outstanding manner by a particularly high activity as pesticides, in particular as insecticides, acaricides and nematicides.

The substances according to the invention thus represent a valuable enrichment of the art.

In the definitions of $R^2$ and $R^3$ in the general formula, optionally substituted alkyl denotes straight chain or branched alkyl having preferably 1 to 20, particularly preferably 1 to 12, in particular 1 to 6 and very particularly preferably 1 to 4 carbon atoms. Examples which may be mentioned are optionally substituted methyl, ethyl, n-propyl, i-propyl, n-butyl, sec-butyl, i-butyl, tert-butyl, n-pentyl, i-pentyl and tert-pentyl.

In the definitions of $R^1$, $R^2$ and $R^3$ in the general formula, straight-chain or branched alkenyl having preferably 2 to 8, particularly preferably 2 to 6 and in particular 2 to 4 carbon atoms denotes the term optionally substituted alkenyl itself or as part of the group alkenyloxy. Examples which may be mentioned are optionally substituted vinyl, allyl, 2-butenyl, 3-butenyl and 1-methylallyl.

In the definition of $R^1$ in the general formulae, the term optionally substituted alkoxy is taken to mean straight-chain or branched alkoxy having preferably 1 to 6, in particular 1 to 4 carbon atoms. Examples which may be mentioned are optionally substituted methoxy, ethoxy, propoxy, butoxy and their isomers, such as, for example, i-propoxy, i-, s- and tert.-butoxy, with particular emphasis on optionally substituted methoxy and ethoxy.

In the definitions $R^1$, $R^2$ and $R^3$ in the general formulae, the term optionally substituted alkinyl itself or as part of the group alkinyloxy is taken to mean straight-chain or branched alkinyl having preferably 2 to 6, particularly preferably 2 to 4 carbon atoms. Examples which may be mentioned are optionally substituted ethinyl, 2-propinyl, 2-butinyl, 3-butinyl and 1-methyl-2propinyl.

In the definitions $R^2$ and $R^3$, optionally substituted cycloalkyl denotes cycloalkyl having preferably 3 to 8, in particular 3, 5 or 6, carbon atoms. Examples which may be mentioned are optionally substituted cyclopropyl, cyclobutyl, cyclopentyl, cyclohexyl and cycloheptyl.

Substituted radicals mentioned in the definition of $R^1$, $R^2$ and $R^3$ can carry one or more than one, preferably 1 to 3, in particular 1 or 2, identical or different substituents. Preferred substituents which may be mentioned for alkyl, alkenyl and alkinyl are: alkoxy having 1 to 4 carbon atoms, such as methoxy, ethoxy, n-propoxy, i-propoxy, n-butoxy, i-butoxy, sec-butoxy, tert-butoxy and halogen.

The radicals alkoxy, alkenyloxy and alkinyloxy can preferably be substituted by halogens, such as fluorine, chlorine, bromine and iodine, in particular fluorine, chlorine and bromine, and by $C_1$–$C_4$-alkoxy.

Preferred substituents which may be mentioned on cycloalkyl are: alkyl having 1 to 4 carbon atoms, such as methyl, ethyl, n-propyl, i-propyl, n-butyl, i-butyl, sec-butyl and tert-butyl, and halogenoalkyl, such as, for example, trifluoromethyl and halogen.

The radicals $R^1$, $R^2$ and $R^3$ are preferably unsubstituted.

In the definition X and $X^1$ in the general formulae and also as substituents for a group, halogen stands for fluorine, chlorine, bromine and iodine, in particular fluorine, chlorine and bromine, in the case of X in particular for chlorine or bromine and in the case of $X^1$ in particular for chlorine.

If $R^2$ and $R^3$ together with the nitrogen atom form a ring, the latter contains 5 to 7, preferably 5 or 6 ring members. The ring can contain 1 to 3 double bonds; preferably, however, it is saturated. Rings which may be mentioned as particularly preferred are the pyrrolidine ring and the piperidine ring.

In the general formulae, $R^1$ preferably stands for $C_1$–$C_4$-alkoxy, in particular methoxy and ethoxy.

In the general formulae, $R^2$ and $R^3$ preferably do not simultaneously stand for hydrogen.

In the general formulae, $R^2$ preferably stands for hydrogen and $R^3$ preferably stands for $C_1$–$C_4$-alkyl.

Preferred thionophosphoramidates of the formula (I) according to the invention are those
in which $R^1$ stands for $C_1$–$C_4$-alkoxy, $C_2$–$C_6$-alkenyloxy and $C_2$–$C_6$-alkinyloxy, which are optionally substituted by halogen and/or $C_1$–$C_4$-alkoxy, $R_2$ and $R_3$ are identical or different and independently of one another stand for hydrogen, for $C_1$–$C_4$-alkyl which is optionally substituted by halogen and/or $C_1$–$C_4$-alkoxy; for cycloalkyl which has 3 to 8 carbon atoms and which is optionally substituted by methyl, ethyl, fluorine and/or chlorine; or for $C_2$–$C_6$-alkenyl and/or $C_2$–$C_6$-alkinyl which are optionally substituted by halogen, and/or $C_1$–$C_4$-alkyl, or together with the nitrogen atom form a 5- to 6-membered, saturated or unsaturated ring and X stands for fluorine, chlorine or bromine (preferably chloride or bromine).

Here, preferred compounds of the formula (I) are those
in which $R^1$ stands for $C_1$–$C_4$-alkoxy which is optionally substituted by halogen or $C_1$–$C_4$-alkoxy, $R^2$ stands for hydrogen, $R^3$ stands for $C_1$–$C_4$-alkyl which is optionally substituted by halogen or $C_1$–$C_4$-alkoxy and X stands for chlorine or bromine.

Particularly preferred thionophosphoramidates of the formula (I) are those
in which $R^1$ stands for $C_1$–$C_4$-alkoxy, $C_2$–$C_3$-alkenyloxy and $C_2$–$C_4$-alkinyloxy which are optionally substituted by fluorine, chlorine, methoxy and/or ethoxy, $R^2$ and $R^3$ are identical or different and independently of one another, stand for hydrogen, for $C_1$–$C_4$-alkyl which is optionally substituted by fluorine, chlorine, bromine, methoxy and/or ethoxy, for cycloalkyl which has 3 to 6 carbon atoms and which is optionally substituted by methyl, ethyl, fluorine and/or chlorine; or for $C_2$–$C_4$-alkenyl and $C_2$–$C_4$-alkinyl which are optionally substituted by fluorine, chlorine, methyl and/or ethyl; or together with the nitrogen atom to which they are bonded stand for piperidyl and pyrrolidinyl, and X stands for fluorine, chlorine and bromine (preferably chlorine or bromine).

Here, preferred compounds of the formula (I) are those
in which $R^1$ stands for $C_1$–$C_4$-alkoxy which is optionally substituted by fluorine, chlorine, methoxy and/or ethoxy, $R^2$ stands for hydrogen, $R_3$ stands for $C_1$–$C_4$-alkyl which is optionally substituted by fluorine, chlorine, bromine, methoxy and/or ethoxy and X stands for chlorine or bromine.

Very particularly preferred thionophosphoramidates of the formula (I) are those
in which $R^1$ stands for methoxy, ethoxy and chloroethoxy (preferably for methoxy and ethoxy), $R^2$ stands for hydrogen, $R^3$ stands for methyl, ethyl, n-propyl, isopropyl, isobutyl, sec-butyl and allyl and X stands for chlorine and bromine.

If, for example, O-(2-bromo-1,1-difluoro-ethyl) ethyl chlorothionophosphate and iso-propylamine are used as starting substances, the course of the reaction of the process according to the invention can be represented by the following equation:

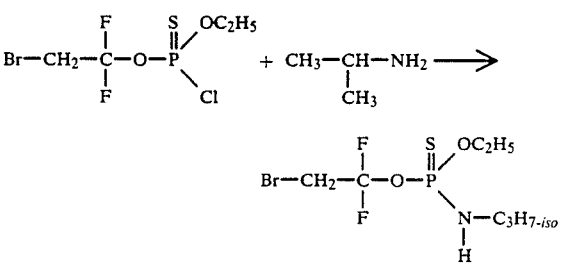

Formula (II) provides a general definition of the O-(1,1-difluoro-2-halogeno-ethyl) halogenothionophosphoric acid diesters to be used as starting substances in the process according to the invention. In this formula (II), X, $X^1$ and $R^1$ preferably, or particularly preferably stand for those radicals which are mentioned above in the definitions of formula (I) or formula (II).

The O-(1,1-difluoro-2-halogeno-ethyl) halogenothionophosphoric acid diesters of the formula (II) are new and form part of the present invention.

The compounds of the formula (II) are obtained when O-(1,1-difluoro-2-halogeno-ethyl) dihalogenothionophosphoric acid esters of the formula

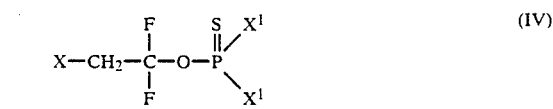

in which

X and $X^1$ have the abovementioned meaning are reacted with alcohols of the formula $$R^1—M \qquad (V)$$

in which $R^1$ has the abovementioned meaning and

M stands for hydrogen or an alkali metal equivalent or alkaline earth metal equivalent (e.g. potassium, sodium or calcium), at room temperature, if appropriate in the presence of an acid acceptor, such as, for example, collidine and if appropriate in the presence of a solvent, such as, for example, ether (cf. DE-OS No. (German Published Specification) 2,629,016 and DE-OS No. (German Published Specification) 2,630,561).

Formula (IV) provides a general definition of the O-(1,1-difluoro-2-halogeno-ethyl) dihalogenothionophosphoric acids to be used as starting substances in the process for the preparation of the compounds of the formula (II). In this formula (IV), X and $X^1$ preferably, or particularly preferably stand for those radicals which are mentioned above in the definitions of the formula (I) or formula (II).

The O-(1,1-difluoro-2-halogeno-ethyl) dihalogenothionophosphoric acids of the formula (IV) are new and form part of the present invention.

The compounds of the formula (IV) are obtained when O-(1,1-difluoro-2-halogeno-ethyl) dihalogenophosphoric acid esters of the formula

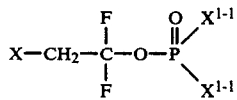  (VI)

in which

X and $X^1$ have the abovementioned meanings, are reacted with thiophosphoryl chloride of the formula $PSCl_3$  (VII)

if appropriate in the presence of a diluent and if appropriate in the presence of a phosphorus sulphide, such as, for example, phosphorus(V) sulphide ($P_2S_5$, $P_4S_{10}$) or 2,4-bis-(4-methoxyphenyl)-1,3,2,4-dithiaphosphetane 2,4-disulphide (Lawesson reagent). Suitable diluents for preparing the new compounds of the formula (IV) are virtually inert organic solvents and also thiophosphoryl chloride.

These preferably include aromatic, optionally halogenated hydrocarbons, such as toluene, xylene, chlorobenzene and o-dichlorobenzene, dichlorotoluene, monochloroxylene and dichloroxylene. Thiophosphoryl chloride is particularly preferred.

The process for the preparation of the new compounds of the formula (IV) is generally carried out at temperatures of between 100° C. and 160° C., preferably at temperatures of between 120° C. and 140° C.

When carrying out the process for the preparation of the compounds of the formula (IV), 1 mol of starting substance of the formula (VI) is reacted with 1 to 20 mols, preferably 1 to 6 mols, of thiophosphoryl chloride and 0.0001 to 0.2 mol, preferably 0.001 to 0.01 mol, of phosphorus(V) sulphide. The reactions are generally carried out under atmospheric pressure.

When carrying out the process for the preparation of the compounds of the general formula (IV), the starting substance of the formula (VI) is brought to reflux together with phosphorus(V) sulphide in one of the solvents mentioned, particularly preferably thiophosphoryl chloride, with the phosphorus oxychloride formed continuously being distilled off. When the reaction is complete, the compounds of the formula (IV), which are obtained as crude products, can be purified in a conventional manner, advantageously by fractional distillation under reduced pressure. They are characterized by the retention index (Kovats index).

Formula (VI) provides a general definition of the O-(1,1-difluoro-2-halogeno-ethyl) dihalogenophosphoric acid esters to be used as starting substances. In this formula (VI), X and $X^{1-1}$ preferably, or particularly preferably stand for those radicals which are mentioned above in the definitions of formula (I).

The compounds of the formula (VI) have been disclosed (DE-OS No. (German Published Specification) 2,507,779).

Thiophosphoryl chloride of the formula (VII) ($PSCl_3$), which is also to be used as a starting substance, is a generally known compound of inorganic chemistry.

The process according to the invention for the preparation of the new compounds of the formula (I) is preferably carried out using diluents.

These include in particular aliphatic or aromatic, optionally halogenated hydrocarbons, such as, for example, pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as dimethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process for the preparation of the new compounds of the formula (I) are all acid-binding agents which can customarily be employed for reactions of this type. Alkaline earth metal hydroxides such as, for example, calcium hydroxide, alkali metal carbonates and alkali metal alkoxides, such as sodium carbonate, potassium carbonate, sodium methoxide, potassium methoxide, sodium ethoxide and potassium ethoxide, furthermore aliphatic, aromatic or heterocyclic amines, for example triethylamine, trimethylamine, dimethylaniline, dimethylbenzylamine, pyridine, collidine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

When carrying out the process for the preparation of the compounds of the formula (I), the reaction temperatures can be varied within a relatively wide range. In general, the process is carried out at temperatures of between 0° C. and 100° C., preferably at temperatures of between 20° C. and 60° C.

In general, the reaction is allowed to proceed under atmospheric pressure. For carrying out the process according to the invention, the reactants are preferably employed in the equimolar ratio. An excess of one or the other component does not provide any essential advantages. The reaction is preferably carried out in one of the solvents mentioned, in the presence of an acid acceptor. Working up of the batch is carried out by customary methods by filtration, washing of the filtrate and distilling off the solvent.

The new compounds are obtained in the form of oils, some of which cannot be distilled without decomposition, but can be freed from the last volatile constituents by so-called "incipient distillation", i.e., by relatively long heating under reduced pressure and at a moderately increased temperature, and purified in this manner. They are characterized by the retention index (Kovats index).

The active compounds are suitable for combating animal pests, preferably arthropods and nematodes, in particular insects and arachnids, which occur in agriculture, in forests, in the protection of stored goods and materials and also in the hygiene field. They are active against normally sensitive and resistant species and also against all or individual stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinthrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example. *Pectinophora gossypiella, Bupalus piniarius, Cheimatobia brumata, Lithocolletis blancardella, Hyponomeuta padella, Plutella maculipennis, Malacosoma neustria, Euproctis chrysorrhnea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa comonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Oliorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanss spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds of the formula (I) according to the invention are distinguished by an excellent insecticidal activity. In particular when applied as soil insecticides, they show an excellent action against grubs, such as, for example, *Phorbia antiqua* grubs, against aphids, such as, for example, *Myzus persicae* and also an excellent action against nematodes, such as, for example, *Meloidogyne incognita.*

The active compounds according to the invention are distinguished by an excellent insecticidal activity, in particular when combating Orthoptera species, such as, for example, *Blattella germmainca* and Coleoptera species, such as, for example, *Sitophilus granarius.*

The active compounds according to the invention can also be applied with very good success for combating hygiene pests, such as, for example, *Musca domestica Diptera, Aedes aegypti Diptera* and *Aedes aegypti* larvae.

The active compounds can, depending on their particular physical and/or chemical properties, be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface active agents, that is emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticide include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

Example I-1

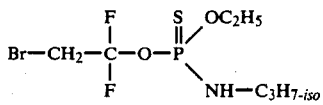

11.1 g (0.19 mol) of isopropylamine are added dropwise at +20° C. to a solution of 22.8 g (0.075 mol) of O-ethyl O-(2-bromo-1,1-difluoro-ethyl) chlorothionophosphate in 200 ml of diethyl ether, and the mixture is stirred for 16 hours at room temperature. The reaction mixture is poured into water, the organic phase is separated off and dried over magnesium sulphate, and the solvent is stripped off under reduced pressure.

16.6 g (68% of theory) of O-ethyl O-(2-bromo-1,1-difluoro-ethyl) N-isopropylthionophosphoramidate having the retention index 1451* are obtained.

The end products of the formula

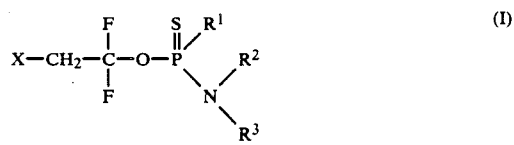

(I)

listed in the following Table 1 are obtained which are analogously to Example (I-1) and with consideration of the instructions in the description of the process according to the invention:

TABLE 1

| Ex. No. | X | $R^1$ | $R^2$ | $R^3$ | Retention Index* |
|---|---|---|---|---|---|
| I-2 | Cl | —OC$_2$H$_5$ | H | —C$_3$H$_7$-iso | 1372 |
| I-3 | Cl | —OC$_2$H$_5$ | H | —CH$_3$ | 1308 |
| I-4 | Cl | —OCH$_3$ | H | —C$_3$H$_7$-iso | 1322 |
| I-5 | Cl | —OCH$_3$ | H | —CH$_3$ | 1256 |
| I-6 | Cl | —OCH$_3$ | H | —CH$_2$—CH=CH$_2$ | 1369 |
| I-7 | Cl | —OCH$_3$ | H | —C$_3$H$_7$-n | 1387 |
| I-8 | Cl | —OC$_2$H$_5$ | H | —C$_2$H$_5$ | 1353 |
| I-9 | Cl | —OC$_2$H$_5$ | H | —C$_3$H$_7$-n | 1435 |
| I-10 | Cl | —OC$_2$H$_5$ | H | —CH$_2$—CH=CH$_2$ | 1419 |
| I-11 | Br | —OC$_2$H$_5$ | H | —C$_4$H$_9$-iso | 1558 |
| I-12 | Br | —OC$_2$H$_5$ | H | —C$_4$H$_9$-sec | 1545 |
| I-13 | Cl | —OCH$_3$ | H | —C$_2$H$_5$ | 1306 |
| I-14 | Cl | —OCH$_3$ | —C$_2$H$_5$ | —C$_2$H$_5$ | 1374 |
| I-15 | Cl | —OCH$_3$ | H | —C$_4$H$_9$-sec | 1412 |
| I-16 | Cl | —OCH$_3$ | H | —C$_4$H$_9$-tert. | 1370 |
| I-17 | Cl | —OCH$_3$ | H | —C$_4$H$_9$-iso | 1432 |
| I-18 | Cl | —OCH$_3$ | —CH$_3$ | —CH$_3$ | 1237 |
| I-19 | Cl | —OCH$_3$ | H | H | |
| I-20 | Br | —OCH$_3$ | H | —C$_3$H$_7$-iso | 1398 |
| I-21 | Br | —OCH$_3$ | H | —C$_3$H$_7$-n | 1473 |
| I-22 | Br | —OCH$_3$ | H | —CH$_2$—CH=CH$_2$ | 1447 |
| I-23 | Br | —OCH$_3$ | H | —C$_4$H$_9$-sec | 1504 |
| I-24 | Cl | —OCH$_3$ | H | —CH$_2$—C≡CH | 1385 |
| I-25 | Cl | —OCH$_3$ | H | —C$_4$H$_9$ | 1486 |
| I-26 | Cl | —OCH$_3$ | H |  | 1420 |
| I-27 | Cl | —OCH$_3$ | H |  | 1613 |

TABLE 1-continued

| Ex. No. | X | R¹ | R² | R³ | Retention Index* |
|---|---|---|---|---|---|
| I-28 | Cl | —OCH₃ | H | —C₅H₁₁-iso | 1536 |
| I-29 | Cl | —OCH₃ | H | —C₅H₁₁ | 1581 |
| I-30 | Cl | —OCH₃ | H | —CH₂—CH(C₂H₅)₂ | 1620 |
| I-31 | Cl | —OC₂H₅ | H | —C₄H₉-sec | 1462 |
| I-32 | Cl | —OC₂H₅ | H | —C₄H₉ | 1530 |
| I-33 | Cl | —OC₂H₅ | H | —C₄H₉-iso | 1479 |
| I-34 | Cl | —OC₂H₅ | H | —C₄H₉-tert. | 1420 |
| I-35 | Cl | —OC₂H₅ | CH₃ | —CH₃ | 1282 |
| I-36 | Br | —OC₂H₅ | H | —C₃H₇ | 1518 |
| I-37 | Br | —OC₂H₅ | H | —CH₃ | 1388 |
| I-38 | Br | —OCH₃ | H | —CH₃ | 1339 |
| I-39 | Cl | —OC₂H₅ | C₂H₅ | —C₂H₅ | 1416 |
| I-40 | Cl | —OCH₃ | H | —CH(C₂H₅)₂ | 1497 |

*The retention indices (Kovats index) were determined on a boiling point phase (dimethylsilicone) by means of gas chromatography.

PREPARATION OF STARTING PRODUCTS

Example II-1

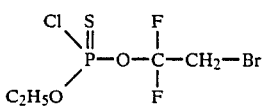

100 ml (1.7 mol) of ethanol are added to a solution of 88.2 g (0.3 mol) of O-(2-bromo-1,1-difluoro-ethyl)dichlothionophosphate in 200 ml of ether with cooling, the mixture is stirred for 16 hours at room temperature and evaporated, the residue is taken up in ligroin, the mixture is washed twice with water, the organic phase is dried over magnesium sulphate, and the solvent is stripped off under reduced pressure.

O-Ethyl O-(2-bromo-1,1-difluoro-ethyl) chlorothionophosphate having the retention index 1242* is obtained in 76% yield.

The compounds of the formula

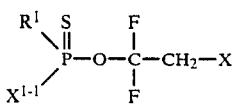

listed in the following Table 2 are also prepared by the method indicated in Example (II-1).

TABLE 2

| Ex. No. | X | X¹⁻¹ | R¹ | Retention Index* |
|---|---|---|---|---|
| II-2 | Cl | Cl | —OCH₃ | 1104 |
| II-3 | Cl | Cl | —OC₂H₅ | 1161 |
| II-4 | Cl | Cl | —OCH₂CH₂Cl | 1362 |
| II-5 | Br | Cl | —OCH₃ | 1180 |

*The retention indices (Kovats index) were determined on a boiling point phase (dimethylsilicone) by means of gas chromatography.

Example (IV-1)

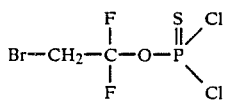

1,667 g (6.0 mol) of O-(2-bromo-1,1-difluoro-ethyl) dichlorophosphate, 3,257 g (19.2 mol) of thiophosphoryl chloride and 32.7 g (0.147 mol) of phosphorus(V) sulphide are heated at 140° C. for 5 days and then distilled. 1,132 g (64.2% of theory) of O-(2-bromo-1,1-difluoro-ethyl) dichlorothionophosphate of boiling point 46° C./0.3 mbar, having the retention index 1119*, are obtained.

The compound of the formula

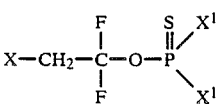

mentioned in the following Table 3 is also obtained by the method indicated in Example (IV-1):

TABLE 3

| Ex. No. | X | X¹ | Retention Index* |
|---|---|---|---|
| IV-2 | Cl | Cl | 1037 |

*The retention index (Kovats index) was determined on a boiling point phase (dimethylsilicone) by means of gas chromatography.

USE EXAMPLES

In the subsequent use examples, the compound mentioned below was employed as comparison compound:

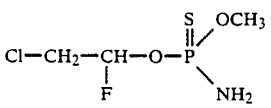

(disclosed in DE-OS (German Published Specification) No. 2,629,016, which corresponds to U.S. Pat. No. 4,159,324).

EXAMPLE A

L Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been destroyed and is 0% if just as many test insects are still alive as in the case of the untreated control.

In this test, for example the compounds of the Preparation Examples I-2, I-3, I-4, I-6 and I-7 showed a degree of effectiveness of 100% at an exemplary concentration of 20 ppm, while the comparison compound resulted in only 0% at the same concentration.

EXAMPLE B

Test insect: *Myzus persicae* Solvent:

Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the destruction figures. It is 100% if all test insects have been destroyed and 0% if just as many test insects are still alive as in the case of the untreated control.

In this test, for example the compound of the Preparation Example I-2 showed an effectiveness of 95% at an exemplary concentration of 10 ppm, while the comparison compound resulted in 0% effectiveness at the same concentration.

EXAMPLE C

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, lettuce is sown and the pots are kept at a greenhouse temperature of 27° C.

After four weeks, the lettuce roots are examined for infestation with nematodes (root galls), and the degree of effectiveness of the active compound is determined in %. The degree of effectiveness is 100% if in infestation is completely avoided and is 0% if the infestation is just as high as in the case of the control plants in untreated soil which has been infested in the same manner.

In this test, for example the compound of the Preparation Example I-2 showed an effectiveness of 100% at an exemplary concentration of 2.5 ppm, while the comparison compound resulted in 0% effectiveness at the same concentration.

EXAMPLE D $LT_{100}$ test for Diptera
Test insects: *Musca domestica*
Number of test insects: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test animals is then introduced into the Petri dish, and the dish is covered with a glass lid.

The condition of the test insects is checked continuously. The time required for a 100% knock-down effect is determined.

In this test, for example the compounds of the Preparation Examples I-2 and I-7 showed an $LT_{100}$ value of 90' at an exemplary concentration of 0.002% and the compounds of the Preparation Examples I-3 and I-5 showed an $LT_{100}$ value of 55' and 75', respectively, at an exemplary concentration of 0.002%, while the comparison compound resulted in an $LT_{100}$ value of 240' at the same concentration.

EXAMPLE E

Test insects: *Blattella germanica*
Number of test insects: 5
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test animals is then introduced into the Petri dish, and the dish is covered with a glass lid.

The condition of the test insects is checked 3 days after the experiments have been set up. The destruction in % is determined. In this context, 100% denotes that all test insects have been destroyed; 0% denotes that no test insects have been destroyed.

In this test, for example the compounds of the Preparation Examples I-2 and I-3 showed a destruction of 100% at an exemplary concentration of 0.002%, while the comparison compound resulted in 0% destruction at the same concentration.

EXAMPLE F

Test insects: *Sitophilus granarius*
Number of test insects: 10
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test animals is then introduced into the Petri dish, and the dish is covered with a glass lid.

The condition of the test insects is checked 3 days after the experiments have been set up. The destruction in % is determined. In this context, 100% denotes that all test insects have been destroyed; 0% denotes that no test insects have been destroyed.

In this test, for example the compounds of the Preparation Examples I-2, I-3, I-5, I-6 and I-7 showed a destruction of 100% at an exemplary concentration of 0.002%, while the comparison compound resulted in a destruction of 30% at the same concentration.

EXAMPLE G

LT$_{100}$ test for Diptera
Test insects: *Aedes aegypti*
Number of test insects: 20
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m$^2$ of filter paper varies, depending on the concentration of the active compound solution. The stated number of test animals is then introduced into the Petri dish, and the dish is covered with a glass lid.

The condition of the test insects is checked continuously. The time required for a 100% knock-down effect is determined.

In this test for example the compounds of the Preparation Examples I-2 and I-3 showed an LT$_{100}$ of 120' at an exemplary concentration of 0.002, while the comparison compound resulted in an LT$_{100}$ of 3$^h$ (50%) at the same concentration.

EXAMPLE H

Mosquito larvae test
Test insects: *Aedes aegypti* larvae
Solvent: 99 parts by weight of acetone
Emulsifier: 1 part by weight of benzylhydroxydiphenyl polyglycol ether To produce a suitable preparation of active compound, 2 parts by weight of active compound are dissolved in 1,000 parts by volume of the solvent, containing the amount of emulsifier stated above. The solution thus obtained is diluted with water to the desired lower concentrations.

The aqueous preparations of active compound are filled into glass vessels and about 25 mosquito larvae are then placed in each glass vessel.

After 24 hours, the destruction in % is determined. 100% means that all larvae have been destroyed. 0% means that no larvae at all have been destroyed.

In this test, for example the compounds of the Preparation Examples I-2, I-3, I-5, I-6 and I-7 showed a destruction of 100% at an exemplary concentration of 0.1%, while the comparison compound resulted in 0% destruction at the same concentration.

It will be understood that the specification and examples are illustrative but not limitative of the present invention and that other embodiments within the spirit and scope of the invention will suggest themselves to those skilled in the art.

We claim:

1. A thinonophosphoric acid amide ester of the formula $$X-CH_2-\underset{\underset{F}{|}}{\overset{\overset{F}{|}}{C}}-O-P\overset{\overset{S}{\|}}{\underset{N\diagdown R^3}{\diagup R^2}}R^1 \quad (I)$$

in which
R$^1$ stands for optionally substituted radicals from the group consisting of alkoxy, alkenyloxy and alkinyloxy,
R$^2$ and R$^3$ are identical or different and independently of one another stand for optionally substituted radicals from the group consisting of alkyl, cycloalkyl, alkenyl and alkinyl, or one of them may stand for hydrogen, and
X stands for halogen.

2. A compound according to claim 1, in which R$^1$ stands for C$_1$-C$_4$alkoxy, C$_2$-C$_6$alkenyloxy and C$_2$-C$_6$-alkinyloxy which are optionally substituted by halogen and/or C$_1$-C$_4$-alkoxy, R$^2$ and R$^3$ are identical or different and independently of one another stand for C$_1$-C$_4$-alkyl which is optionally substituted by halogen and/or C$_1$-C$_4$-alkoxy; for cycloalkyl which has 3 to 8 carbon atoms and which is optionally substituted by methyl, ethyl, fluorine and/or chlorine; or for C$_2$-C$_6$-alkenyl and C$_2$-C$_6$-alkinyl which are optionally substituted by halogen and/or C$_1$-C$_4$-alkyl, or one of them may stand for hydrogen, and X stands for fluorine, chlorine or bromine.

3. A compound according to claim 1, in which R$^1$ stands for C$_1$-C$_4$-alkoxy, C$_2$-C$_3$-alkenyloxy or C$_2$-C$_4$-alkinyloxy which are optionally substituted by fluorine, chlorine, methoxy and/or ethoxy, R$^2$ and R$^3$ are identical or different and independently of one another stand for C$_1$-C$_4$-alkyl which is optionally substituted by fluorine, chlorine, bromine, methoxy and/or ethoxy, for cycloalkyl which has 3 to 6 atoms and which is optionally substituted by methyl, ethyl, fluorine and/or chlorine; or for C$_2$-C$_4$-alkenyl and C$_2$-C$_4$-alkinyl which are optionally substituted by fluorine, chlorine, methyl and/or ethyl; or one of them may stand for hydrogen, and
X stands for fluorine, chlorine and bromine.

4. A compound according to claim 1, in which
R$^1$ stands for C$_1$-C$_4$-alkoxy which is optionally substituted by halogen,
R$^2$ stands for hydrogen,
R$^3$ stands for C$_1$-C$_4$-alkyl which is optionally substituted by halogen and
X stands for chlorine or bromine.

5. A compound according to claim 1,
in which
R$^1$ stands for C$_1$-C$_4$-alkoxy which is optionally substituted by fluorine or chlorine,
R$^2$ stands for hydrogen,
R$^3$ stands for C$_1$-C$_4$-alkyl which is optionally substituted by fluorine, chlorine or bromine, and
X stands for chlorine or bromine.

6. A compound according to claim 1, in which
R$^1$ stands for methoxy, ethoxy or chloroethoxy
R$^2$ stands for hydrogen, R³ stands for methyl, ethyl, n-propyl, isopropyl, isobutyl, sec-butyl and allyl and X stands for chlorine and bromine.

7. A compound according to claim 1, wherein such compound is O-ethyl O-(2-bromo-1,1-difluoro-ethyl) N-isopropylthionophosphoramidate of the formula

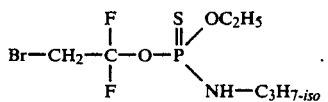

8. A compound according to claim 1, wherein such compound is O-ethyl O-(2-chloro-1,1-difluoro-ethyl) N-isopropylthionophosphoramidate of the formula

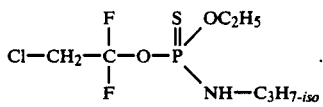

9. An insecticidal, acaricidal or nematicidal composition comprising an insecticidally, acaricidally or nematicidally effective amount of a compound according to claim 1 and a diluent.

10. A method of combating insects, acarids or nematodes which comprises applying to such insects, acarids or nematodes, or to an insect, acarid or nematode habitat, an insecticidally, acaricidally or nematicidally effective amount of a compound according to claim 1.

11. The method according to claim 10, wherein such compound is
O-ethyl O-(2-bromo-1,1-difluoro-ethyl) N-isopropylthionophosbhoramidate or
O-ethyl O-(2-chloro-1,1-difluoro-ethyl) N-isopropylthionophosphoramidate.

12. An O-(1,1-difluoro-2-halogeno-ethyl) halogenothionophosphoric acid ester of the formula

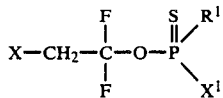

in which
R¹ stands for optionally substituted radicals from the group consisting of alkoxy, alkenyloxy and alkinyloxy, and
X and X¹ each independently stands for halogen.

13. An O-(1,1-difluoro-2-halogeno-ethyl) halogenothionophosphoric acid diester of the formula

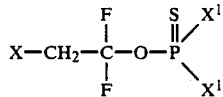

in which
X and X¹ each independently stands for halogen.

* * * * *